United States Patent [19]
Kletschka et al.

[11] 3,931,821
[45] Jan. 13, 1976

[54] SUTURE BRIDGES

[75] Inventors: Harold D. Kletschka; Edson H. Rafferty, both of Minneapolis, Minn.

[73] Assignee: Bio-Medicus, Inc., Minnetonka, Minn.

[22] Filed: Aug. 26, 1974

[21] Appl. No.: 500,689

Related U.S. Application Data

[63] Continuation-in-part of Ser. No. 309,466, Nov. 24, 1972, Pat. No. 3,831,608.

[52] U.S. Cl. .............................. 128/335; 24/129 R
[51] Int. Cl.[2] ........................................ A61B 17/04
[58] Field of Search ............ 128/334 R, 335, 335.5, 128/326, 327; 24/129 R, 129 B, 129 C, 137, 138; 124/23

[56]         References Cited
             UNITED STATES PATENTS

| 815,264 | 3/1906 | Chambers ...................... 128/334 R |
| 1,306,369 | 6/1919 | Bell .................................. 24/129 B |
| 1,928,536 | 9/1933 | Heinlen et al...................... 24/138 R |
| 2,292,140 | 8/1942 | Lofgren ............................ 24/129 D |
| 3,541,591 | 11/1970 | Hoegerman...................... 128/335 |
| 3,831,608 | 8/1974 | Kletschka et al. .................. 128/335 |

Primary Examiner—Dalton L. Truluck
Attorney, Agent, or Firm—Merchant, Gould, Smith, Edell, Welter & Schmidt

[57]             ABSTRACT

The disclosure is directed to a surgical bridge for supporting incision sutures under continuous tension. The bridge is elongated in shape, including two feet which engage the surface of a patient's skin on opposite sides of an incision, and which are connected by a bridge portion that overlies the incision. The bridge further includes a pair of resiliently flexible cantilevered arms each of which defines a suture support point elevated from the skin surface to preclude cutting or slicing of the patient's skin by the suture. In one embodiment, the suture bridge is made from two interlocking pieces, which enables the advantageous usage of two materials having different resilience, and also simplifies manufacture of the device. Improved structure is also disclosed in conjunction with the suture bridge for effecting tying or securing of a suture end to the bridge quickly and easily.

24 Claims, 11 Drawing Figures

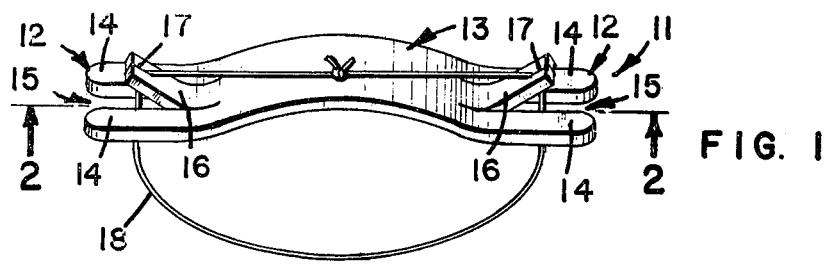
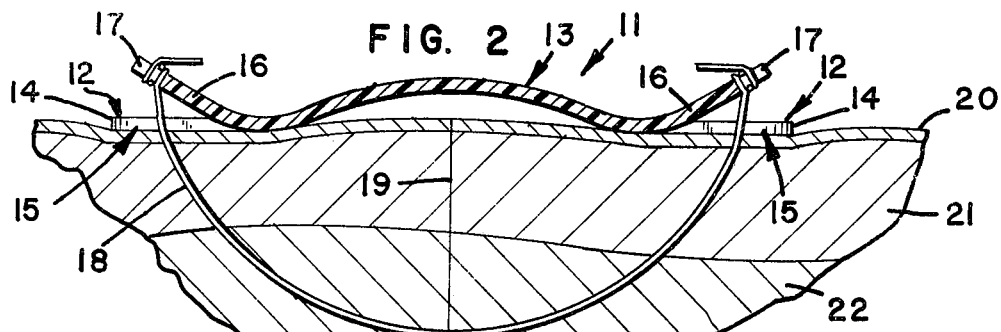
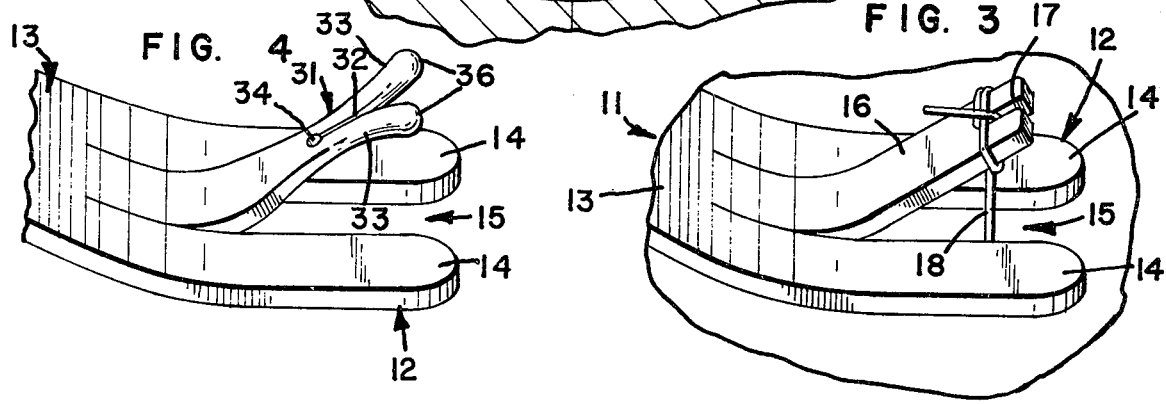
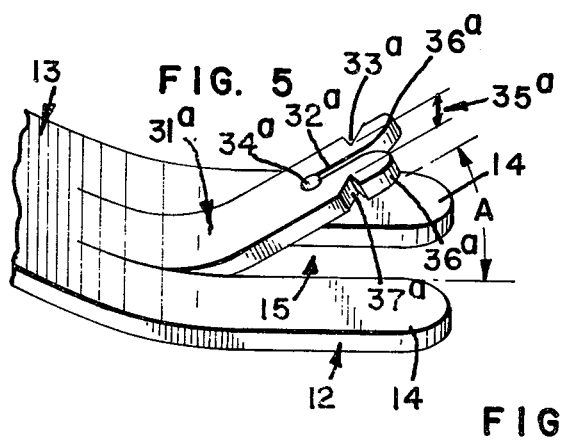
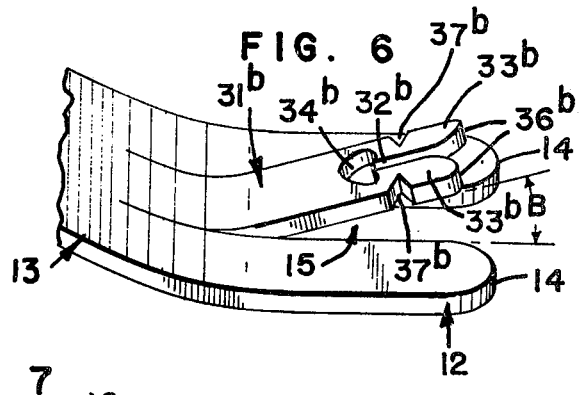

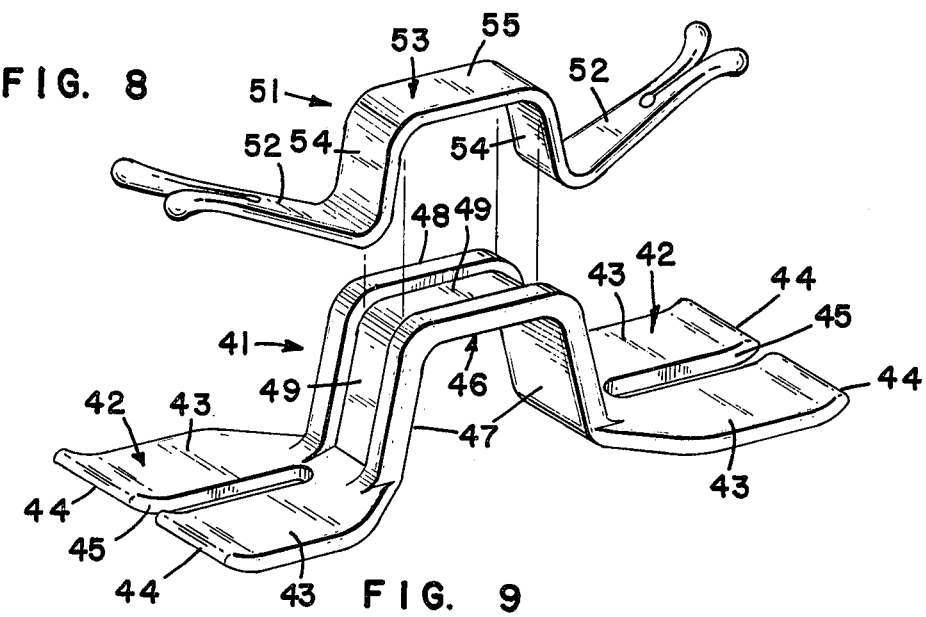
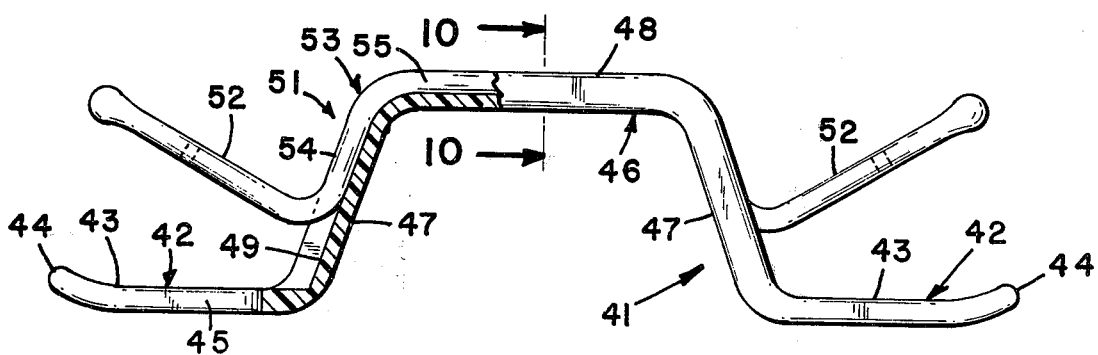
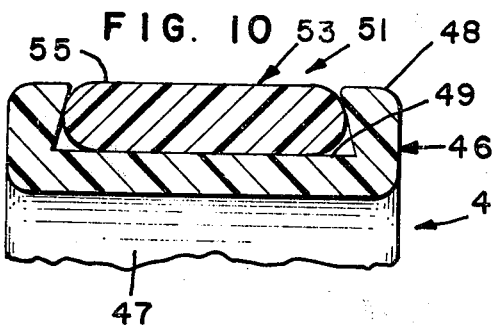
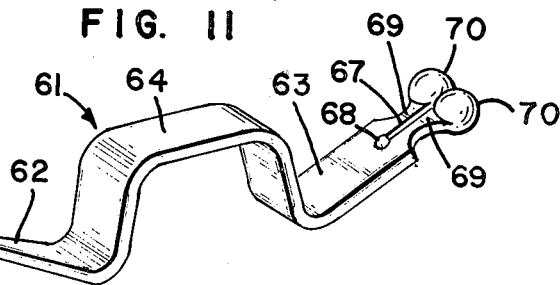
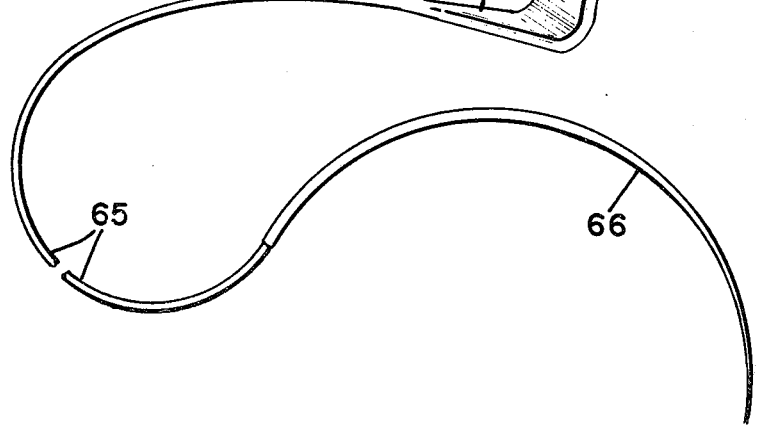

SUTURE BRIDGES

This is a continuation-in-part of our copending application entitled "Suture Bridges" which was filed on Nov. 24, 1972 under Ser. No. 309,466, which issued as U.S. Pat. No. 3,831,608 on Aug. 27, 1974.

The invention relates to surgical bridges for supporting incision sutures under continuous tension.

Surgical devices of this general type have existed for some time in a number of different forms. For example, see the devices disclosed in U.S. Pat. No. 815,264 issued to Joseph E. Chambers on Mar. 13, 1906; U.S. Pat. No. 1,852,098 issued to Alfred W. Anderson on Apr. 5, 1932; and U.S. Pat. No. 3,014,483, which issued on Dec. 26, 1961 to Horace F. McCarthy. With such devices, an incision closing surgical stitch is formed by inserting the suture through the incision under the skin with a surgical needle in the known manner, placing the bridge over the incision relative to the suture, bringing the suture ends around the respective bridge ends and tying them at the middle under the requisite tension.

One problem that has accompanied the formation of surgical stitches with existing devices is cutting or slicing of the patient's skin by the suture itself as swelling of the incision occurs during the healing process. Such swelling tends to force the bridge outwardly, which increases suture tension until the adjacent skin gives way and is cut or slit. The same end effect is also caused by pressured movement of the bridge (as by swelling, for example) which carries the suture laterally with it until the skin gives way. No matter how they occur, skin cuts or slits are a source of major irritation to the patient, and they increase the possibility of infection before the wound has healed completely which can result in the formation of scars.

Our inventive surgical bridge alleviates the problems of excessive suture tension and resulting skin cuts through the regulation of suture tension and suspension of the suture relative to its point of entry into the skin. More specifically, our improved suture bridge comprises an elongated bridge member having end or foot portions joined by a bridge or connecting portion. The foot portions are constructed to engage the surface of a patient's skin on opposite sides of an incision, and the connecting portion is constructed to bridge the incision and directly or indirectly support a suture over the incision. The improved bridge further comprises a resiliently flexible cantilevered arm for each of the foot portions, each arm defining an elevated suture support point which causes the suture to be suspended over the point of entry into the patient's skin. This suture suspension, coupled with appropriately sized openings or slots in the foot portions below through which the suture passes, insures that the patient's skin will not be sliced or cut throughout the incision healing process, notwithstanding the degree of swelling or accidental movement of the bridge relative to the incision and suture.

In one embodiment, the suture bridge is constructed in two pieces: a lower bridge member which includes the foot portions joined by a bridge portion, and an upper bridge member consisting of the cantilevered arms joined by a connecting portion. The connecting portion of the upper bridge member mateably engages the bridge portion of the lower bridge member. Depending on the application, the upper and lower bridge members may be constructed to separably interlock, or they may be permanently fused or bonded together. This two piece construction is particularly advantageous in the manufacture of the cantilever arm-type suture bridge, since the upper and lower bridge members are individually simple to fabricate.

Constructing the upper and lower bridge members for interlockable separation gives rise to a number of advantages. For example, the upper bridge member can be made of a different material than that of the lower bridge member, thus permitting the cantilevered arms to be more resilient and thereby better compensate for swelling during the incision healing process, whereas the foot portions can be somewhat less resilient to provide better support for the suture stitch. The separable construction also enables the lower bridge member to be made of material which is compatible with skin tissue, whereas this requirement is not necessary for the upper bridge member which does not contact the patient's skin. Further, the separable construction permits replaceability of either of the bridge components relative to the other.

Another improvement in our suture bridge resides in the inclusion of structure which permits the free end of a suture to be tied to the bridge quickly and easily. Tying a knot with the free suture ends has long represented a problem to surgeons in the incision suturing procedure. Although this is not ordinarily a major problem to the surgeon, it is quite time consuming; and an improperly tied suture can not only result in discomfort to the patient but can also have an adverse effect on proper healing of the incision. To this end, we incorporate in one or both cantilevered arms of our suture bridge structure which permits the surgeon to tie-off the suture extremely quickly and to complete each suture stitch in a uniform manner. This is accomplished by forming a longitudinal bifurcating slot in the cantilevered arm, extending from the arm end to an inner point within the arm to define a pair of leg members which are resiliently movable relative to each other. Preferably, the cross sectional size of the suture approximates the width of the bifurcating slot, permitting simple entry of the suture into the slot. The bifurcating slot is enlarged at its extreme inner point to a size which is larger than the suture. The leg members are notched or reduced in lateral dimension between the slot enlargement and the extreme end of the cantilevered arm. As such, the suture can be brought through the bifurcating slot to the enlarged region or aperture, and then wrapped tightly around the resilient legs to squeeze them together and close at least a portion of the bifurcating slot. The end or tail of the suture is then introduced into the slot from the end until it frictionally engages the inside surface of the legs where they are squeezed together, thus securing the suture in place.

We further contemplate the provision of an individual precut suture and needle for each surgical bridge which may be integrally formed therewith, to eliminate needless repetition in taking surgical stitches and to insure maximum convenience and simplicity to the physician in carrying out his surgical duties.

Other structural features and advantages of our inventive surgical bridges will become apparent from the description below in conjunction with the accompanying drawings.

BRIEF DESCRIPTION OF THE DRAWINGS

FIG. 1 is a perspective view of the surgical bridge for supporting incision sutures under proper tension;

FIG. 2 is an enlarged sectional view of the suture bridge of FIG. 1 over an incision with a suture in place, taken along the line 2—2 of FIG. 1;

FIG. 3 is an enlarged perspective view of one end of the suture bridge of FIG. 1, showing structure for accomplishing suture tie-off;

FIGS. 4–6 are views similar to that of FIG. 3 showing three different embodiments of improved structure for securing the free end of a suture or the like;

FIG. 7 is an enlarged fragmentary view in top plan of the suture securing structure of FIG. 4;

FIG. 8 is an exploded perspective view of a suture bridge constructed from two interlocking pieces;

FIG. 9 is an enlarged view in side elevation of the suture bridge of FIG. 8 with the interlocking pieces mateably engaged, portions thereof shown in section;

FIG. 10 is an enlarged fragmentary sectional view taken along the line 10—10 of FIG. 9; and FIG. 11 is a perspective view of an alternative embodiment of the upper suture bridge piece of FIG. 8 with a suture and needle integrally formed therewith.

DESCRIPTION OF THE PREFERRED EMBODIMENTS

FIGS. 1–3 disclose a suture bridge 11 which is elongated in shape and broadly comprises end or foot portions 12 joined by a bridge or connecting portion 13. The foot portions are adapted to engage a patient's skin on opposite sides of an incision, and each specifically comprises a pair of longitudinally extending projections 14 spaced apart to define an elongated slot 15 therebetween. In this particular embodiment, each of the slots 15 is formed by punching out a supporting tab 16 which bends upwardly and away from the bridge portion 13 in cantilever fashion. The extreme end of each tab 16 has a friction slit 17 formed therein which is sized to receive and frictionally retain any portion of a suture 18. As described, the tabs 16 and slits 17 define elevated support points for the suture 18 which overlie slots 15, and the slots 15 extend endwardly beyond these support points to preclude engagement of the suture 18 at its point of entry into the skin.

Connecting portion 13 is formed with a gentle curvature in this particular embodiment permitting it to arch incision 19 (FIG. 2), which extends through a patient's skin 20 and layers 21 and 22 of deeper tissue. As used herein, "incision" is intended to encompass wounds, lacerations and the like which disrupt normal tissue integrity, as well as openings made for surgical purposes.

Bridge 11 may be made from any material suitable for surgical accessories of this type, examples of which are stainless steel, nylon and teflon. Of primary importance to the construction of the bridge 11, whatever material from which it is made, is its ability to flex under varying degrees of suture tension, which is caused by swelling of the tissues surrounding incision 19 during the healing process. The flexibility of suture bridge 11 permits it to resiliently bend in a manner which compensates for such swelling, thereby precluding suture tension from becoming excessive to the point of cutting or otherwise damaging the skin. This significant feature of the suture bridge 11 also works conversely; i.e., as the swelling of the skin surrounding incision 18 decreases, any loosening within the suture is automatically tightened by resilient flexibility of the bridge 11 so that proper suture tension is maintained and the surgical stitch continues to carry out its intended purpose.

Formation of a surgical stitch to close an incision 19 is accomplished by introducing the suture 18 through the skin 20 and tissues layers 21, 22, utilizing the bridge 11 so that the suture 18 is suspended between the aforementioned elevated support point and the skin 20. Because each of the elevated suture support points directly overlies its associated slot 15, the suture 18 is disposed essentially normal to the skin at the point of entry and is not engaged by any portion of the bridge 11. This significantly reduces the likelihood of skin tears or cuts, even if swelling of the tissue surrounding incision 19 is appreciable, or if the bridge 11 is accidentally moved.

Tying of the surgical stitch may be in the manner shown in FIG. 1; i.e., by tying the suture 18 at the top of bridge or connecting portion 13 after bringing the suture ends around and through slits 17 of tabs 16. Preferably, tabs 16 are constructed to resiliently flex and bend downwardly with increasing suture tension as swelling occurs, in the manner described above. Alternatively, and with reference to FIGS. 2 and 3, suture 18 may simply be wrapped around the tab 16 and ultimately through slit 17 so that the surgical stitch is held in place without tying. It will be apparent that the surgeon may simply release the surgical stitch for removal or adjustment purposes simply by grasping the free end of suture 18 and removing it from the tab 16.

FIGS. 4 and 7 depict improved structure for accomplishing the securing or tying of the suture end. In the enlarged fragmentary perspective view of FIG. 4, the suture bridge has identical projections 14 for engaging the patient's skin in support of the bridge. With this improved tying structure, however, the cantilevered tab or arm is modified significantly, and bears the general reference numeral 31. More specifically, the cantilevered arm 31 has a bifurcating slot 32 formed therein which extends longitudinally from the extreme end of the arm 31 to an inner point therein to define a pair of leg members 33. Preferably, the width or lateral dimension of bifurcating slot 32 approximates the cross sectional dimension of the suture 18 with which it is used.

It is of importance that the legs 33 be resiliently movable relative to each other. This can be accomplished through a desired choice of material from which the cantilevered arm 31 is made, length of the slot 32 and dimensional parameters of the legs 33 themselves. As will become apparent below, the objective in making the leg members resiliently moveable is to permit them to be squeezed together without undue difficulty.

An aperture 34 is formed through the cantilevered arm 31 at the extreme end of bifurcating slot 32. In this particular embodiment, aperture 34 specifically comprises a round bore. However, as used herein, the term "aperture" is intended to encompass openings of various shapes which extend through the cantilevered arm 31, as well as a simple enlargement of the bifurcating slot 32 at its extreme inner point. In this regard, the important structural relationship is for the aperture to have a lateral dimension (with respect to the longitudinal dimension of the cantilevered arm 31 and bifurcating slot 32) which is greater than the smallest lateral dimension (width) of the bifurcating slot 32. As such, the aperture 34 remains open even with the legs 33 squeezed together, thus preventing the aperture 34 from frictionally engaging or binding that portion of a suture 18 passing therethrough.

As is shown in FIG. 7, the legs 33 are squeezed together by wrapping the suture 18 around the legs in a region between the aperture 34 and the end of the cantilevered arm 31. To facilitate this wrapping of suture, and to hold it in place, the leg members 33 define a region of laterally reduced outer dimension, which is represented by the numeral 35 in FIG. 7. In the embodiment of FIGS. 4 and 7, such region of reduced outer dimension is defined simply by the gentle curvature of the outside surface of each of the legs 33. Stated otherwise, the longitudinal side of each leg 33 which is disposed opposite the bifurcating slot is generally concave in shape.

To facilitate entry of the suture 18 into the bifurcating slot 32, the lateral dimension or width of the slot 32 increases as the slot approaches the extreme end of the cantilevered arm 31, as particularly shown in FIG. 7. This can be accomplished by cutting the slot in such manner, or by causing the leg members 33 to diverge at their extreme end, as is the case in this embodiment. It is also desirable for the extreme end of leg members 33 to be rounded, as at 36, which reduces the likelihood of snagging or unwanted movement of the suture bridge. In this embodiment, the extreme ends 36 of leg members 33 are bulbous in shape.

In use, the surgeon grasps the free suture end, either by hand or instrument and brings it through the bifurcating slot 32 to the aperture 34, retaining a length adequate for wrapping. As shown in FIG. 7, the suture end is then wrapped around the leg members 33 in the region 35, thus causing the leg members 33 to be squeezed together and reducing the width of bifurcating slot 32 or entirely closing a portion of it. The "tail" of the suture 18 is then introduced into the slot 32, where it is frictionally engaged by the inner surfaces of the leg members 33 where they are squeezed together.

As is apparent, tying or securing the suture in this manner completely obviates the necessity of tying a knot with the free suture ends, and is substantially simpler, quicker and more secure than knot tying. The use of this suture tying structure also provides the additional significant advantage of being able to quickly release the suture 18, either for purposes of removal or tension adjustment.

The significance of the aperture, and its size relationship to that of the bifurcating slot, resides in the fact that the portion of the suture which is initially introduced into the slot does not cause the leg members to separate due to its thickness. In other words, in the absence of an aperture which is larger in cross sectional size than that of the suture used, the suture itself separates the leg members and precludes them from frictionally retaining the suture "tail" when it is brought into the slot.

Depending on the degree of resilience of the leg members 33 and the overall size of the aperture 34, sutures of various sizes can be successfully used.

FIG. 5 shows an alternative embodiment of the improved suture tying structure shown in FIGS. 4 and 7, with like components bearing like reference numerals with addition of the letter a. In the embodiment of FIG. 5, the cantilevered arm 31a is generally similar in size and shape to the tab 16 of bridge 11 (see FIG. 3 in particular). Cantilevered arm 31a has a bifurcating slot 32a, which defines leg members 33a, and terminates in an aperture 34a. In this embodiment, the bifurcating slot 32a increases in lateral dimension as it approaches the extreme end of the cantilevered arm 31a to facilitate entry of the suture.

The outer side of each leg 33a (i.e., the side disposed opposite the bifurcating slot 32) is essentially straight. The outer side of each leg 33a is therefore notched, as at 37a, to define the region 35a of reduced lateral dimension; and accordingly, the suture is wrapped around and into these notches 37a. The extreme ends 36a of the legs 33a are rounded.

In the embodiment of FIG. 6, the cantilevered arm 31b is essentially the same as cantilevered arm 31a, with the exception of the aperture 34b. In this embodiment, the aperture 34b is recessed laterally and longitudinally toward the end of the cantilevered arm 31b, relative to the point of communication of slot 32b and aperture 34b, and on opposite sides of the slot 32. In the specific form of this embodiment, the aperture 34b is heart-shaped. These recessed areas on opposite sides of the slot 34b advantageously prevent the suture from being accidentally removed from the aperture 34b once it has been introduced.

The respective embodiments of FIGS. 5 and 6 also point out the desirability of controlling the angles of the cantilevered arm relative to the supporting foot portion and skin. For example, the cantilevered arm 31a defines an angle A with its associated foot portion, and cantilevered arm 31b defines a smaller angle B with its associated foot portion. The selection of a suture bridge having a particular angle between the arm and foot portion is in accordance with the application; i.e., the size and nature of the incision, its location, etc.

FIGS. 8–10 depict a suture bridge of two-piece construction. More specifically, the disclosed suture bridge comprises a lower bridge member 41 and an upper bridge member 51. Lower bridge member 41 consists of foot portions 42 interconnected by a bridge portion 46. Each of the foot portions in turn consists of a pair of longitudinally oriented foot members 43 each of which is essentially flat except for its extreme outer end 44, which is turned up slightly and rounded to preclude patient discomfort in the event of substantial suture pressure. Each of the foot members 43 is relatively wide, defining a substantial cross sectional area on its undersurface to better distribute pressure arising from suture tension. A longitudinal slot or opening 45 extends longitudinally inwardly between the foot members 43, the slot 45 being similar to and having the same purpose of the slot 15 of bridge 11.

As particularly shown in FIG. 9, the bridge portion 46 is angular as distinguished from curved, consisting of converging walls 47 interconnected by a flat top section 48. A dovetailed recess 49 is formed on the top side of bridge portion 46, extending longitudinally through both converging walls 47 and the top section 48.

Upper bridge member 51 consists of cantilevered arms 52 joined together by a connecting portion 53. Each of the cantilevered arms 52 is identical to the cantilevered arm 31 of FIG. 4 insofar that the suture tying structure is concerned. The connecting portion 53 conforms generally in shape to the bridge portion 46, consisting of converging side walls 54 and a flat top section 55. With specific reference to the sectional view of FIG. 10, the thickness of connecting portion 53 generally corresponds to the depth of dovetailed recess 49. The width of connecting portion 53 is chosen for interlocking engagement with the recess 49; i.e., its width lies between the largest and smallest lateral dimensions of the recess. The edges of connecting portion 53 are rounded to facilitate its entry into the dovetailed recess.

As described, it will be appreciated that the lower and upper bridge members 41, 51 mateably engage in an interlocking relationship. The converging side walls 54 of upper bridge member 51 are somewhat shorter than the corresponding side walls 47 of lower bridge member 41, so that the cantilevered arms 52 are spaced above the associated foot portions 42 and define a desired angle therewith. The interlocking or mateable construction is particularly advantageous since it permits materials of different resiliency to be used for the respective upper and lower bridge members 41, 51. For example, it may be desirable for the cantilevered arms 52 to be quite flexible in a particular applicaton, whereas the foot portions 42 should be more rigid to provide the necessary bridge support. Different materials for the upper and lower bridge members may also be necessary where the lower bridge member to be compatible with skin tissue. The two-piece construction also lends itself to replaceability of either of the bridge members. In addition, the bridge members 41, 51 are more easily fabricated individually than is the equivalent one piece device.

FIG. 11 is an alternative embodiment of the upper bridge member 51. The modified bridge member which bears the general reference numeral 61, includes dissimilar cantilevered arms 62, 63 joined by a connecting portion 64 which is essentially the same as the connecting portion 53.

Rather than defining suture tying structure, cantilevered arm 62 is integrally connected with the suture 65, thus eliminating one of the two suture securing steps. The suture 65 is in turn integrally connected with a needle 66. In this embodiment, the blunt end of the needle 66 is hollow and the free end of the suture is inserted and connected by crimping or swaging. Alternatively, the modified upper bridge member 61, the suture 65 and needle 66 can be integrally formed with a single material.

Cantilevered arm 63 includes suture securing structure similar to that of the embodiment of FIGS. 4 and 7. The structure includes a bifurcating slot 67 terminating in an aperture 68, and which defines leg members 69. The concavity of the outer side of the legs 69 is somewhat more extreme than that of the leg members 33. The leg members 69 terminate in essentially spherical tips 70 which themselves define the increasing lateral dimension of the slot 67 at the point of suture entry.

It will be appreciated that the modified upper bridge member 61 enables the surgeon to form a surgical stitch with a single tie-off procedure as described in connection with FIGS. 4–7. The needle 66 is snipped off or otherwise removed after the stitch has been taken. The bridge member 61 is particularly suited to single use, disposable construction. The companion lower bridge member can also be fabricated for a single use, or constructed for more permanent use with replaceable upper bridge members.

We claim:
1. A surgical bridge for supporting incision sutures under tension comprising:
   a. an elongated lower bridge member having first and second foot portions joined by a bridge portion constructed to bridge an incision, the foot portions being constructed to engage the surface of a patient's skin on opposite sides of the incision;
   b. an elongated upper bridge member having first and second arm portions joined by a connecting portion;
   c. and means associated with at least one of said lower and upper bridge members for mateably interlocking the upper bridge member with the lower bridge member;
   d. each of said arm members extending from the connecting portion in cantilever fashion with the extreme end of the arm members defining an elevated suture support point which overlies and is spaced from said opening in the associated foot portion.

2. The device defined by claim 1, wherein said means mateably interlocks the connecting portion of the upper bridge member with the bridge portion of the lower bridge member.

3. The device defined by claim 1, wherein said mateable interlocking means comprises:
   a. a dove-tailed recess on the top of said bridge portion and extending longitudinally thereof;
   b. said connecting portion having a width and depth chosen for interlocking engagement within said dove-tailed recess.

4. The device defined by claim 3, wherein the width of said connecting portion lies between the largest and smallest lateral dimensions of the dove-tailed recess.

5. The device defined by claim 3, wherein the edges of said connecting portion are rounded to facilitate entry thereof into the dove-tailed recess.

6. The device defined by claim 1, wherein at least one of said arm members defines a suture tying device comprising:
   a. a bifurcating slot extending longitudinally from the end of the arm member to an inner point thereof to define a pair of leg members, the leg members being resiliently movable relative to each other and capable of being squeezed together;
   b. an aperture formed through the arm member at said inner point and communicating with the bifurcating slot, the aperture having a lateral dimension greater than the smallest lateral dimension of the slot, whereby the aperture remains open with the resilient leg members squeezed together;
   c. and said leg members defining a region of laterally reduced outer dimension between said inner point and said end, whereby said suture length can be wrapped around the leg members at said reduced area to squeeze the leg members together.

7. The device defined by claim 6, wherein the lateral dimension of the slot increases at said end to facilitate entry of the suture into the slot.

8. The device defined by claim 6, wherein the leg members diverge at said end to facilitate entry of the suture into the slot.

9. The device defined by claim 6, wherein the extreme ends of the leg members are bulbous in shape.

10. The device defined by claim 6, wherein the longitudinal side of each leg member which is disposed opposite the bifurcating slot is generally concave in shape to define said region of laterally reduced outer dimension.

11. The device defined by claim 6, wherein the aperture is circular in shape.

12. The device defined by claim 6, wherein each of said arm members defines said suture tying device.

13. The device defined by claim 6, wherein the other of said arm members is integrally connected with a suture.

14. A surgical bridge for supporting incision sutures under tension comprising:
   a. an elongated bridge member having first and second foot portions joined by a bridge portion constructed to bridge an incision, the foot portions being constructed to engage the surface of a patient's skin on opposite sides of the incision;
   b. each of said foot portions having an opening through which a suture may pass;
   c. first and second arm members for the first and second foot portions, respectively, each arm member extending longitudinally from the bridge portion in cantilever fashion with its extreme end defining an elevated suture support point which overlies and is spaced from said opening in the associated foot portion;
   d. at least one of said arm members defining a suture tying device, comprising
      1. a bifurcating slot extending longitudinally from the end of the arm member to an inner point thereof to define a pair of leg members, the leg members being resiliently movable relative to each other and capable of being squeezed together;
      2. an aperture formed through the arm member at said inner point and communicating with the bifurcating slot, the aperture having a lateral dimension greater than the smallest lateral dimension of the slot, whereby the aperture remains open with the resilient leg members squeezed together;
      3. and said leg members defining a region of laterally reduced outer dimension between said inner point and said end, whereby said suture length can be wrapped around the leg members as said reduced area to squeeze the leg members together.

15. The device defined by claim 14, wherein each of said arm members defines said suture tying device.

16. The device defined by claim 14, wherein the other of said arm members is integrally connected with a suture.

17. The device defined by claim 14, wherein the lateral dimension of the slot increases at said end to facilitate entry of the suture into the slot.

18. The device defined by claim 14, wherein the leg members diverge at said end to facilitate entry of the suture into the slot.

19. The device defined by claim 14, wherein the extreme ends of the leg members are bulbous in shape.

20. The device defined by claim 14, wherein the longitudinal side of each leg member which is disposed opposite the bifurcating slot is generally concave in shape to define said region of laterally reduced outer dimension.

21. The device defined by claim 14, wherein the side of each leg member disposed opposite the bifurcating slot is notched to define said region of laterally reduced outer dimension.

22. The device defined by claim 14, wherein the aperture is circular in shape.

23. The device defined by claim 14, wherein the aperture is recessed laterally and longitudinally toward said end relative to the slot-aperture point of communication on opposite sides of the slot.

24. The device defined by claim 23, wherein said aperture is heart-shaped.

* * * * *